(12) United States Patent
Moos et al.

(10) Patent No.: US 6,528,019 B1
(45) Date of Patent: Mar. 4, 2003

(54) MEASURING TRANSFORMER FOR DETECTING HYDROCARBONS IN GASES

(75) Inventors: Ralf Moos, Friedrichshafen (DE); Plog Carsten, Markdorf (DE)

(73) Assignee: Dornier GmbH, Friedrichshafen (DE)

( * ) Notice: Subject to any disclaimer, the term of this patent is extended or adjusted under 35 U.S.C. 154(b) by 0 days.

(21) Appl. No.: 09/508,294

(22) PCT Filed: Jun. 24, 1999

(86) PCT No.: PCT/DE99/01838

§ 371 (c)(1),
(2), (4) Date: Jul. 20, 2001

(87) PCT Pub. No.: WO00/03238

PCT Pub. Date: Jan. 20, 2000

(30) Foreign Application Priority Data

Jul. 9, 1998 (DE) .......................... 198 30 709

(51) Int. Cl.⁷ .............................. G01N 31/12
(52) U.S. Cl. ............... 422/94; 422/83; 422/88; 422/98; 422/50
(58) Field of Search ............. 422/94, 98, 50; 252/519.15; 73/23.32; 338/34; 204/426; 60/274

(56) References Cited

U.S. PATENT DOCUMENTS

| | | | | |
|---|---|---|---|---|
| 4,454,494 A | | 6/1984 | Williams et al. | |
| 4,677,414 A | * | 6/1987 | Yates | 338/34 |
| 4,988,970 A | * | 1/1991 | Hafele et al. | 338/34 |
| 5,071,626 A | * | 12/1991 | Tuller | 422/98 |
| 5,175,997 A | * | 1/1993 | Blanke, Sr. | 60/274 |
| 5,203,165 A | * | 4/1993 | Wild et al. | 60/274 |
| 5,352,353 A | * | 10/1994 | Schonauer et al. | 204/426 |
| 5,952,555 A | * | 9/1999 | Mobius | 73/23.32 |

FOREIGN PATENT DOCUMENTS

| EP | 78300466.6 | 10/1978 |
|---|---|---|
| EP | 93203531.4 | 12/1993 |

* cited by examiner

*Primary Examiner*—Jill Warden
*Assistant Examiner*—Brian Sines
(74) *Attorney, Agent, or Firm*—Crowell & Moring LLP

(57) ABSTRACT

A measuring transformer for detecting hydrocarbons in gaseous media with two resistive oxygen sensors whose electrical resistance is essentially independent of temperature with one of the two resistive oxygen sensors being catalytically activated for reducing hydrocarbons.

6 Claims, 4 Drawing Sheets

MEASURING TRANSFORMER FOR DETECTING HYDROCARBONS IN GASES

BACKGROUND OF THE INVENTION

Field of the Invention

The invention relates to a measure transformer for detecting hydrocarbons in gases.

DISCUSSION OF THE BACKGROUND

Increasingly strict environmental legislation is forcing automobile manufacturers to develop and use exhaust emission control systems, usually catalytic converters, with ever better conversion rates in order to maintain the government-specified maximum values of emitted emissions such as nitrogen oxides, carbon monoxide, or unburned hydrocarbons. At the same time, it is required that the function of the exhaust emission control systems be monitored continuously during operation and that defective function be indicated, ranging from exceeding the limits as a result of aging phenomena of the catalyst to a total failure of the $\lambda$-probe that controls the combustion stoichiometry. For this so-called on-board diagnosis (OBD), an exhaust sensor located downstream of the exhaust emission control system is required that monitors the function of the exhaust emission control system during operation and whose sensor signal serves as a basis for determining the state of the exhaust emission control system.

With a four-stroke engine operated at $\lambda=1$ (1 represents the fuel-air mixture), the emissions are drastically reduced by a three-way catalyst. While it is not difficult to meet the nitrogen oxide and carbon monoxide limits, theoretically unburned hydrocarbons (HC) pose the greatest problems. Malfunction of the exhaust emission control system is indicated only when the HC concentration in the exhaust increases.

There are many ways to diagnose an exhaust emission control system. Several patents such as DE 34 13 760, U.S. Pat. No. 5,740,676, U.S. Pat. No. 5,467,594, and DE 42 09 136 for example as well as the literature references [1] and [2] cited as examples propose providing $\lambda$-probes upstream and downstream of the catalytic converter. The oxygen storage capacity and hence indirectly the function of the catalytic converter can be determined from a comparison of the amplitude fluctuations in the probe output signals upstream and downstream of the catalytic converter. Such methods are already used in mass production. Another frequently discussed method is diagnosis of the exhaust emission control system by means of one or more temperature sensors. In this case, it is the reaction heat resulting from the conversion of the hydrocarbons in the untreated exhaust that is detected. Examples will be found in [3]–[7] or in DE 42 01 136. Direct determination of the hydrocarbon concentration in the purified exhaust by means of an HC sensor would be much simpler and more precise than determination of values that depend only indirectly on emissions.

Such direct HC sensors can incorporate for example HC measurement by means of a surface ionization detector [8], but this method depends to a significant degree on the gas throughput, the type of hydrocarbons, and the oxygen content of the exhaust.

Another type of HC sensor is the familiar catalytic sensor (also known as the pellistor) described here using the example in EP 0 608 122. For such sensors, oxygen is always necessary to burn the hydrocarbons so that the output signal depends largely upon the oxygen content of the exhaust. In addition, very exact temperature control and measurement are required since the electrical resistance of a temperature-dependent part is measured. Therefore, such a sensor principle is unsuited for use in the exhaust line.

A sensor design that consists of an oxygen generator, oxygen diffusion zone, HC sensor zone, and at least two temperature control zones and is therefore very complex is described in U.S. Pat. No. 5,689,059. This sensor is suitable for exhaust but requires electrical terminals in considerable numbers. In addition, this sensor, which in reality a sensor system, requires very complex and costly control and regulating electronics so that it cannot be used for the broad mass market.

Hydrocarbon sensors using planar technology are less expensive to manufacture.

DE 0 046 989 proposes an HC sensor based on tungsten oxide made by the planar technique which can be used only at room temperature.

Pt-MOSiC sensors based on silicon carbide are proposed in [9] for use in motor vehicles. However, the operating mechanism is not easy to understand and the signals are dependent not only on the hydrocarbon but also on oxygen and temperature. Manufacture of planar structures on SiC is also costly and therefore cannot be used for the motor vehicle mass market.

Widely used, inexpensive sensors are made on a ceramic substrate from $SnO_2$. Examples include EP 0 444 753 or EP 0 603 945. In this sensor principle, the electrical sensor resistance changes with the HC concentration in the gas. Sensors of this type are used in large numbers as sensitive elements in gas warning systems and their functional mechanism is widely known. An attempt to use such sensors in an automobile is described in [10] and [11]. Unfortunately, these sensors lose their gas-sensitive properties at temperatures above several hundred degrees Celsius and change their resistance only with the oxygen partial pressure of the gas. The long-term stability of these sensors is not guaranteed either.

Resistive sensors based on metal oxides which have been proposed more frequently as an oxygen-detecting element but not as an HC sensor are likewise manufactured using planar technology and are suitable for use in exhaust. In the resistive principle, the electrical resistance of the sensitive material is used as a measured value. For example, DE 37 23 051 proposes doped titanates, zirconates, or stanates as resistive oxygen-sensitive materials which are applied according to DE 37 23 052 using thick film technology to a ceramic substrate. DE 42 02 146, DE 42 44 723, and DE 43 25 183 propose compositiones based on cuprates manufactured using thick film technology as oxygen-sensitive materials. DE 44 18 054 mentions lanthanum ferrites doped with alkaline earths for the same purpose. Such multiple metal oxides which are usually present in the perovskite structure have the advantage of increased chemical stability and greater long-term stability over the sensors made of simple metal oxides, $TiO_2$ [10] for example, that have been in use for a long time. All of these oxygen sensors however have a typical temperature curve of the electrical resistance according to an exponential function typical for semiconducting metal oxides, in other words the sensor output signal depends not only on the oxygen partial pressure of the exhaust but on the sensor temperature as well. Hence, for such oxygen exhaust sensors, an exact temperature measurement is linked to a costly electronic regulation or a reference that is not exposed to the exhaust and is kept at a constant temperature must be integrated in the substrate which is also expensive and leads to problems with long-term stability.

The series connection of two resistive oxygen sensors which in addition to their oxygen dependence have a temperature dependence with different temperature coefficients of the specific electrical resistance, is proposed in DE 38 33 295. In addition, a compensating resistance must also be included. However, in this method, despite the high costs, a temperature independence of the sensor resistance can be achieved only in a very narrowly delimited oxygen partial pressure range.

A resistive oxygen sensor that is temperature-independent only at a certain oxygen partial pressure is described in a portion of EP 0 062 994. In DE 19 744 316, an oxygen sensor is proposed made of a material in which the oxygen partial pressure range of temperature independence can be varied by deliberate variation (doping) of the layer material.

Typical HC sensors manufactured using planar technology are characterized by the following typical arrangement. On the underside of an electrically insulating substrate a heater and/or a temperature measuring device in the form of a resistance thermometer is mounted. Then, on the substrate surface, an electrode structure is provided that meets the special requirements and a functional layer is mounted on top of this structure.

In EP 0 426 989 and in [12], the electrode structure has a so-called interdigital capacitor arrangement (IDC). Zeolites are proposed as the functional layer. Dependent on the temperature, the complex electrical resistance of the functional layer varies very selectively in this case with the hydrocarbon concentration in a gas. In [13] $Ga_2O_3$ is proposed as the material for a resistive planar HC sensor. However, a significant dependence of the sensor output signal on temperature is reported here as well. This sensor reacts to oxygen [12] especially above 900° C.

In another method for producing planar sensors, a $ZrO_2$ layer is applied to the substrate and two different electrodes with different electrical potentials are added. The differential voltage between the two different electrodes is then the measurement signal. This method is described in great detail in [14]. A variation is described in U.S. Pat. No. 5,352,353 and DE 41 02 741 and DE 41 09 516. It is readily apparent that the output signal from such sensors depends to a large extent upon temperature and naturally on oxygen partial pressure of the exhaust as well. Additional cross sensitivities to hydrogen for example, are also present.

In DE 42 28 052, a sensor is described that consists of a combination of two individual resistive oxygen sensors, with one of the two sensors being provided with a catalytically active coating. As a result, the incompleteness of the combustion in the engine can be determined from the differential signal of the two sensor elements. Such a sensor has the disadvantage that it is not temperature-compensated, in other words as in all resistive oxygen sensors, the output signal is primarily temperature-dependent and depends only secondarily on gas concentration.

To remedy this situation, DE 195 31 202 proposes a bridge arrangement consisting of at least four individual sensor elements of which two are—and two are p-conducting, arranged so that one branch of the bridge is activated catalytically and that an—and a p-conducting sensor are arranged in each branch of the bridge circuit. In addition to the considerable cost and technical problems involved, in applying at least four different materials in addition to the electrical terminals in layers on a substrate compatibly with one another, this system does not produce a sensor that is temperature-independent for all oxygen partial pressure ranges.

The disadvantage of all planar HC sensors is the considerable temperature dependence of the sensor output signal which requires either exact temperature regulation or exact temperature measurement followed by electronic compensation of the signal or the materials that differ only by a cumbersome arrangement of different materials on a support can be partially compensated.

SUMMARY OF THE INVENTION

Hence, the goal of the present invention is to provide a measuring transformer for HC detection which eliminates the stated disadvantages of the prior art, especially temperature dependence.

This goal is achieved by the measuring transformer according to claim 1. Advantageous embodiments of the invention as well as special applications of the measuring transformer according to the invention are the subject of additional claims.

According to the invention, two resistive oxygen sensors are provided, one of them provided with a catalytically active layer for reducing hydrocarbons. Both oxygen sensors are characterized by an essentially temperature-independent characteristic. The electrical resistances of the two sensors are measured and both the hydrocarbon concentration and the oxygen partial pressure of the gas to be analyzed can be determined from the two measured values. Since the oxygen partial pressure is measured as well, the available oxygen dependence of the catalytically non-activated oxygen sensor can be calculated.

Both oxygen sensors are held at the same working temperature. As a result of the temperature independence of the sensor output signal, only limited requirements need to be imposed on temperature measurement and regulation. Depending on the desired accuracy, they can even be eliminated. A resistance heater can be provided as a heater for example. It is also possible to provide heating by hot gases which are available in the vicinity of the hydrocarbon detection, for example the exhaust gases from a furnace or an internal combustion engine.

The measurement transformer according to the invention is preferably made using thick film or thin film technology with the two oxygen sensors being mounted on an electrically insulating substrate.

Preferred areas of application for the measurement transformer according to the invention are:

Measurement of the hydrocarbon concentration in the exhaust from a furnace or heating system. In addition, the output signal from the non-activated resistive oxygen sensor can be used to detect the oxygen content in the exhaust from the furnace or heating system.

Measurement of the concentration of flammable gases, especially hydrocarbons, in the ambient air.

Measurement of the hydrocarbon concentration in the exhaust from an internal combustion engine. The output signal of the activated resistive oxygen sensor can be used in addition for detecting the fuel-air mixture in the exhaust from the engine.

Diagnosis of an exhaust emission purification system in the exhaust from an internal combustion engine. In addition, the output signal from the activated resistive oxygen sensor can be used to detect the oxygen-air mixture of the internal combustion engine.

Performing mixture control in an internal combustion engine.

BRIEF DESCRIPTION OF THE DRAWINGS

The invention will now be described below using a few preferred embodiments as examples, with reference to drawings. The embodiments described serve only to explain the invention and are not intended to imply that they represent a limitation of the invention to these special embodiments.

DETAILED DESCRIPTION OF THE PREFERRED EMBODIMENTS

Figure 1:
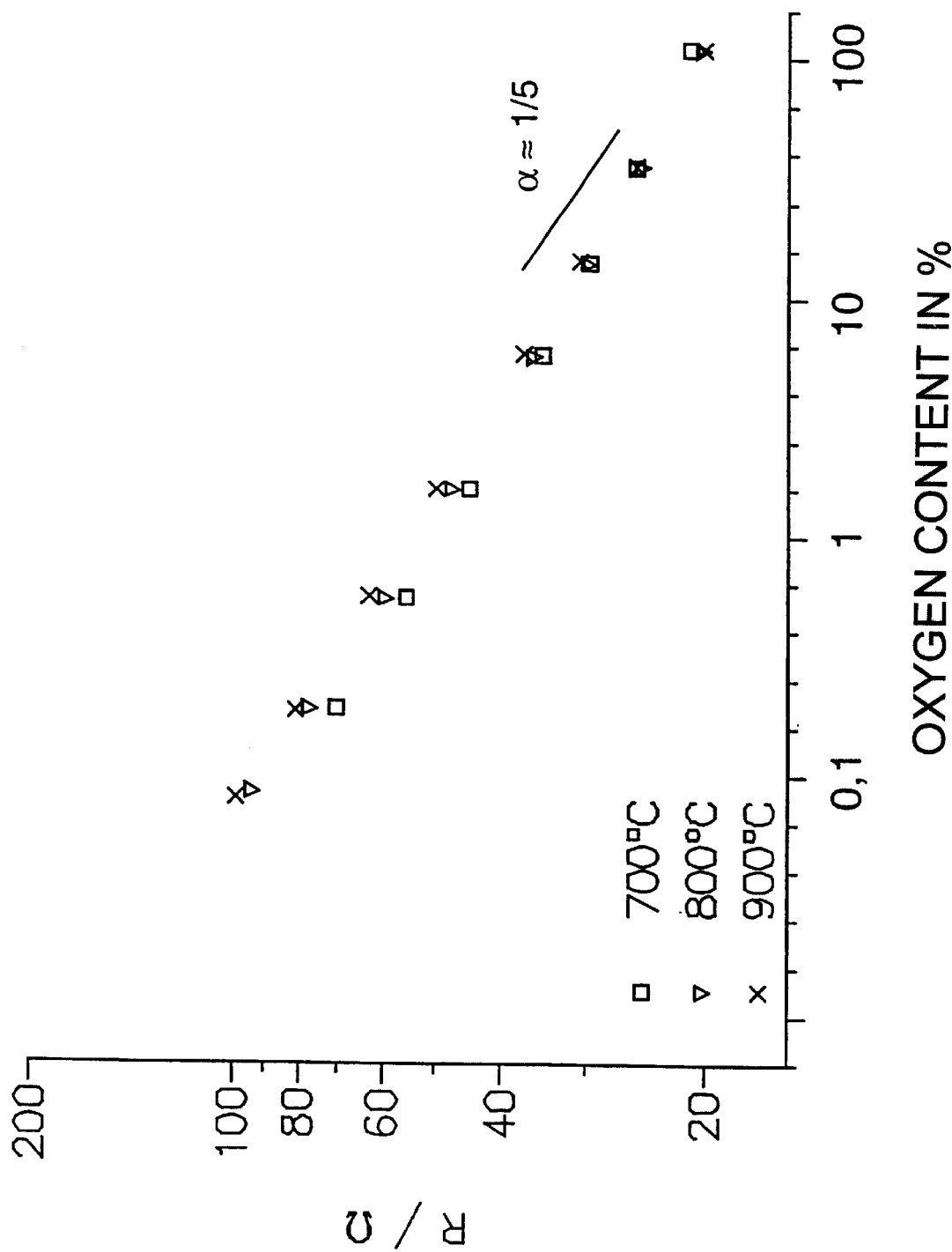
Figure 2:
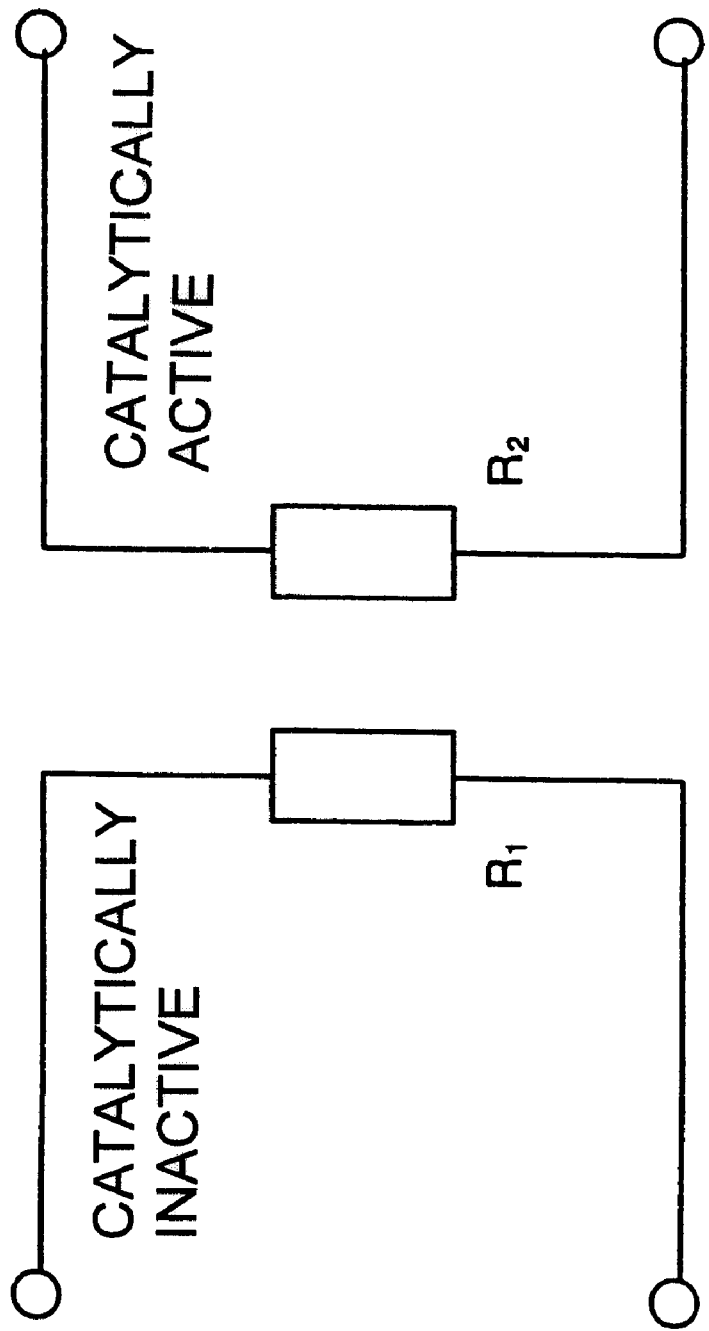
Figure 3:
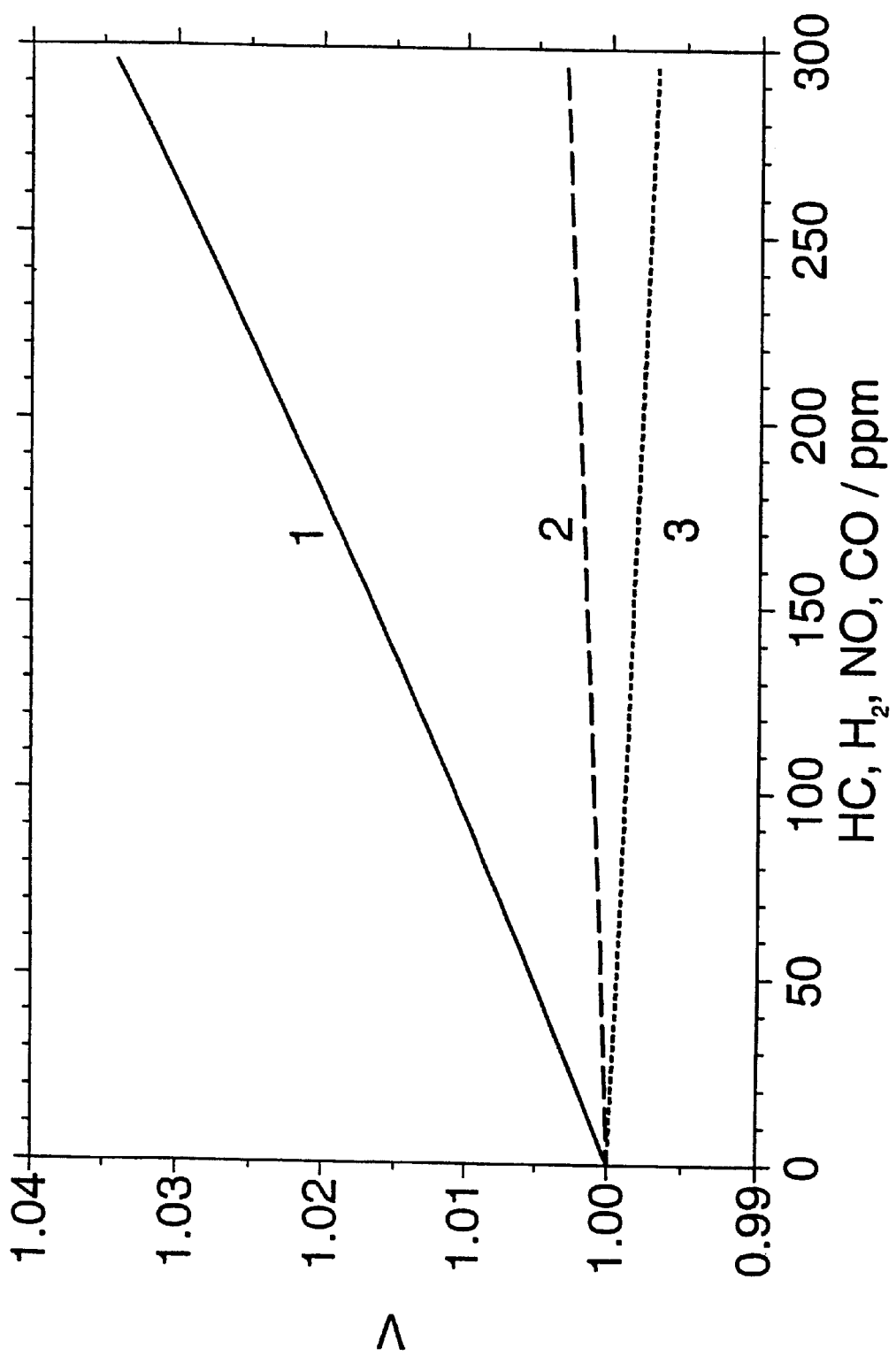
Figure 4:
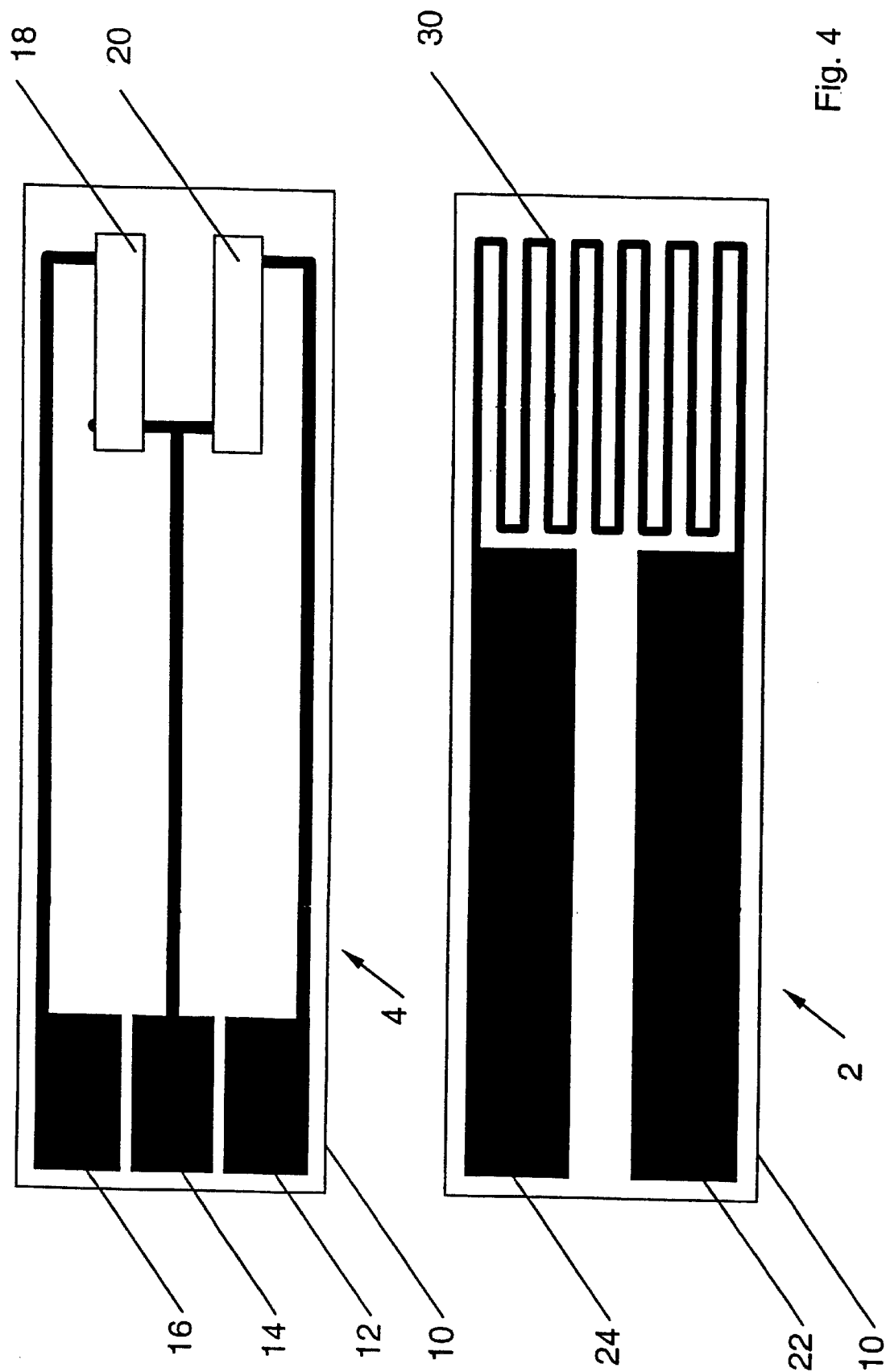

FIG. 1 shows the typical curve of the electrical resistance of a temperature-independent resistive oxygen sensor using thick film technology which can be used in the measuring transformer according to the invention;

FIG. 2 shows a sample embodiment of the measuring transformer according to the invention in a schematic view;

FIG. 3 shows the sensitivity of a measuring transformer according to the invention and its cross sensitivity to hydrogen, carbon monoxide, and nitrogen monoxide;

FIG. 4 shows the technical implementation of a measuring transformer according to the invention as in FIG. 2.

In EP 0 062 994, a resistive oxygen sensor that is temperature independent at a certain oxygen partial pressure is shown. In DE 197 44 316, an oxygen sensor is proposed in which the oxygen partial pressure range during temperature independence can be varied by changing the layer material. A typical curve from DE 197 44 316 is shown in FIG. 1. The sensor resistance varies almost independently of temperature with oxygen partial pressure ($pO_2$). The dependence is approximately $R \sim pO_2^{-a}$, with $a \approx \frac{1}{5}$. For the function of the electrical resistance over the oxygen partial pressure, Equation 1 applies approximately:

$$R_x \approx R_{x,0} \times pO_2^{-1/5} \qquad (1)$$

Here, the subscript X assumes the values 1 and 2. Its significance is explained below. The value of the prefactor $R_{x,0}$ depends on the geometry of the sensor.

According to the invention, two resistances, both of which can be described by Equation 1, are combined with one another as shown in FIG. 2 for example. In the embodiment shown there, the measuring transformer according to the invention has four terminals for measuring the two resistances R1, R2. However, three terminals will suffice if the two resistances R1 and R2 have a common terminal. The second resistance (subscript X=2) is activated catalytically according to the invention so that hydrocarbons arriving at it react immediately. The oxygen partial pressure at its surface is then reduced. The heat released during the reaction does not affect the sensor resistance, however, since the resistance does not depend upon the temperature. The non-activated resistance (subscript X=1) accordingly measures the free oxygen while the activated resistance measures the hydrocarbon content present following the reaction of the hydrocarbons with oxygen. The combustion $C_mH_n$ can serve as an example: The reaction of the hydrocarbons requires oxygen according to Equation 2:

$$C_mH_n + \left(m + \frac{n}{4}\right)O_2 \rightarrow mCO_2 + \frac{n}{2}H_2O$$

For propane (m=3, n=8), eight oxygen molecules would be consumed per $C_3H_8$ molecule if complete reaction can take place on the surface of the sensor. The oxygen partial pressure is defined over part z of the oxygen molecules on the total number of molecules according to Equation 3:

$$pO_2 = z \times p_{total} \qquad (3)$$

In determining the hydrocarbon concentration, the basis used is that the oxygen partial pressure on catalytically active resistance 2 is $pO_{2,2}$, $$\left[z - \left(m + \frac{n}{4}\right) \times c_{HC}\right] \times p$$

total and is therefore lower than the oxygen partial pressure on the non-activated resistance 1, $pO_{2,1}$. For the relationship between the oxygen partial pressures and the concentration of the hydrocarbons $C_{HC}$, Equation 4 therefore applies:

$$pO_{2,2} = \left(1 - \frac{\left(m + \frac{n}{4}\right) \times c_{HC}}{z}\right) \times pO_{2,1}$$

With m and n known, from knowledge of the two oxygen partial pressures, the hydrocarbon concentration in the gas can be determined. The variables m and n and comparable values that describe the oxygen requirement for combustion can be determined from experiments or calculated with a known exhaust composition.

A simple evaluation possibility is offered by the formation of the two sensor resistances R1 and R2, with $$V = \frac{R_1}{R_2}$$

for the relationship $$V = \frac{R_{1,0}}{R_{2,0}} \times \left(1 - \frac{\left(m + \frac{n}{4}\right) \times c_{HC}}{z}\right)^{\frac{1}{5}}$$

A curve of this kind is plotted in FIG. 3. It is clear how the sensitivity to hydrocarbons (curve 1, solid) stands out from the cross sensitivities to hydrogen and carbon monoxide (curve 2, dashed) or nitrogen monoxide (curve 3, dotted).

However, it is not necessary to plot the ratio; instead, the differential signal between the two resistances or another possible method for evaluating the different resistance curves may be selected.

In the above explanation of the measurement principle, it was assumed for the sake of simplification that only one specific hydrocarbon is present in the gas to be investigated. The invention is not limited to this. Even with several different hydrocarbons, it offers usable results about the presence of hydrocarbons. One application for this is the use of the measuring transformer according to the invention in order to diagnose the function of an exhaust emission control system connected upstream of an internal combustion engine.

As already mentioned, individual signals from the two oxygen sensors can also be used for separate evaluation in order to obtain additional information through the oxygen content for example.

A material suitable for both oxygen sensors is metal oxides, especially those that have a perovskite ($ABO_3$) structure; both the A-locations and the B-locations can be occupied by more than one type of ion. A typical representative is multiply doped $Sr(TiFe)O_3$.

It should also be pointed out that the two oxygen sensors do not have to be made of the same material.

The sketch of a technical implementation of a measuring transformer according to the invention using thick film technology is shown in FIG. 4. A heating and measurement resistance structure made of platinum for example is mounted on underside 2 of a substrate 10 which consists in this simplified sketch of leads and contact surfaces 22 and 24 with an impedance as low as possible as well as a zone with a high resistance 30. In this range, the sensor is heated. On the top 4 of substrate 10 there are three leads 12, 14, and 16 which likewise have a contact area applied to them. They consist of an electrically conducting material which is ideally catalytically inactive. According to the invention, two resistive temperature-independent oxygen sensors 18 and 20 are mounted on the leads, with one of the two oxygen sensors being additionally provided with a catalytically active and electrically nonconducting layer.

To produce a measuring transformer according to the invention on the basis of complex metal oxides, the oxides, carbonates, and/or oxycarbonates of the metals that occur in the sensitive material are added in stoichiometric ratio, mixed intimately, ground up in an organic solvent, dried, and burned and the metal oxide powder thus obtained is processed to form a paste. This paste is applied to a preferably electrically insulating substrate and burned. The electrodes required to measure the electrical resistance are attached either before or after the metal oxide paste is burned.

In order to make a measuring transformer according to FIG. 4, one can proceed in detail as follows. First of all, a ceramic powder that has the desired sensitive properties is produced. For this purpose, the starting materials (oxides, carbonates, nitrates, or oxycarbonates for example) are measured to obtain the desired stoichiometric ratio. A typical batch of approximately 50 g raw powder is then processed in a grinder together with a grinding medium which can be a solvent such as cyclohexane or isopropanol for example, with grinding balls (for example, made of agate, 10 mm in diameter, 50 in number or a smaller ball diameter with a correspondingly larger number of balls) and mixed for 1–4 hours in a planetary ball mill. The ground material thus mixed is dried, separated from the balls, loaded into a crucible, and burned in a furnace in an atmosphere of air at 1200° C. for 15 hours. The cooled powder then has the desired material composition as can be proven for example by X-ray diffractometry. Powder burned in this way must be comminuted further by means of another grinding step in order to have the powder grain size distribution suitable for the remainder of the manufacturing process. A typical grinding process as described above can be carried out but 7–10 balls each having a diameter of 20 mm should be chosen. The powder can be comminuted in an attrition mill or in an annular ball mill. The powder, dried and separated from the balls, can then be processed further to form a paste that can be used for screen printing. Then, suitable connectors (made of gold or platinum for example, are printed on a substrate (for example, made of $Al_2O_3$ or $ZrO_2$) by screen printing in order to be able to measure the sensor resistance. These connectors are typically stoved in an atmosphere of air. Then the sensor layers are printed and likewise stoved. A heating layer can also be added to the back of the sensor. One of the two oxygen sensors thus produced is given a gas permeable, porous, catalytically active, but electrically nonconducting coating. Leads are attached to the electrodes of the measuring connectors and the heating connectors. The design can be as shown in FIG. 4. A suitable housing provided with electrical leads ensures mechanical stability and protects the sensor.

References

[1] Albrecht F., Braun H.-S., Krauss M., Melsberger D.: BMW six-cylinder technology for TLEV and OBDII requirements in the USA, MTZ 57, 10 (1996), 552–557.

[2] Blumenstock K. U.: "Everything on board?" Auto & Technik (in mot), (1993), 135–138.

[3] Cal W., Collings N.: A Catalytic Oxidation Sensor for the On-Board Detection of Misfire and Catalyst Efficiency. SAE paper 922248 (1992).

[4] Pelters S., Schwarzenthal, D., Maus W., Swars H., Brück R.: Alternative Technologies for Studying Catalyst Behaviour to Meet OBDII Requirements. SAE paper 932854 (1993).

[5] Theis J.: Catalytic Converter Diagnosis Using the Catalys Exotherm. SAE paper 942058 (1994).

[6] Kato N., Ikoma N., Nishikawa S.: Exhaust Gas Temperature Sensor for OBDII Catalyst Monitoring. SAE paper 960333 (1996).

[7] Koltsakis G., Stamatelos A.: Concept for catalytic converter monitoring using reaction heat determination. MTZ 58, 3 (1997), 178–184.

[8] Cal W., Collings N.: An Unburnt Hydrocarbon Measurement by Means of a Surface Ionization Detector. SAE paper 910254 (1991).

[9] Arbab A., Spetz A., Lundström I.: Evaluation of gas mixtures with high-temperature gas sensors based on silicon carbide. Sensors and Actuators B 18–19, (1994), 562–565.

[10] Eastwood P., Claypole T., Watson J.: Development of tin dioxide based exhaust sensors. IEE Conference Publication. London No. 346, 8th Conference on Automotive Electronics (1991), 19–23.

[11] Howarth D., Micheli A.: A Simple Titania Thick Film Exhaust Gas Oxygen Sensor. SAE paper 840140 (1984).

[12] Plog C., Maunz W., Kurzweil P., Obermeier E., Scheibe C.: Combustion gas sensitivity of zeolite layers on thin film capacitors. Sensors and Actuators B 24–25, (1995), 403–406.

[13] Fleischer M., Bernhardt K., Feltz A.: Introduction to gas sensorics. New sensor materials open up new markets. Siemens-Matsushita Components, Publication (1995).

[14] Somov S., Reinhardt G., Guth., Göpel W.: Gas analysis with arrays of solid state electrochemical sensors: Implications to monitor HCs and $NO_x$ in exhausts. Sensors and Actuators B 35–36, (1996), 409–418.

What is claimed is:

1. A measuring transformer for detecting hydrocarbons in gaseous media, said transformer comprising:

two resistive oxygen sensors whose electrical resistance is essentially temperature-independent, wherein one of said two resistive oxygen sensors is catalytically activated to reduce hydrocarbons; and a device for measuring said electrical resistance of each of said two oxygen sensors;

said oxygen sensors each comprise one of metal oxides present in perovskite structure or a structure that resembles perovskite, wherein the metal oxide consists of a compound with one of the following compositions:

$$(Sr_{1-n}N_n)_{1-a}M_aTi_{1-z}Fe_zO_{3-d}$$

or

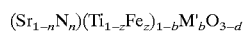

$$(Sr_{1-n}N_n)(Ti_{1-z}Fe_z)_{1-b}M'_bO_{3-d}$$

or

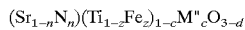

or

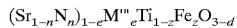

where,
- N is strontium (Sr), barium (Ba), calcium (Ca), magnesium (Mg), zinc (Zn), cadmium (Cd), mercury (Hg), lead (Pb), or radium (Ra) or a mixture of two or more thereof;
- Sr is strontium;
- M stands for an element of the lanthanides (numbers 57 to 71 in the periodic system of the elements) or for yttrium (Y), indium (In), or thallium (Tl) or for a mixture of two or more thereof;
- Ti is titanium;
- Fe is iron;
- O is oxygen;
- n is a number between zero and one;
- a, b, c or e are numbers larger than or equal to zero and smaller than or equal to one-half;
- z is a number larger than or equal to one-tenth and smaller than or equal to six-tenths;
- d is the oxygen deficit that results depending on the composition from the electroneutrality condition;
- M' is phosphorus (P), vanadium (V), chromium (Cr), manganese (Mn), arsenic (As), niobium (Nb), antimony (Sb), tantalum (Ta), molybdenum (Mo), tellurium (Te), or tungsten (W) or a mixture thereof;
- M" ist aluminum (Al), scandium (Sc), gallium (Ga), cobalt (Co), nickel (Ni) or a mixture of two or more of these elements;
- M''' is lithium (Li), sodium (Na), potassium (K), rubidium (Rb), cesium (Cs), copper (Cu), or silver (Ag) or a mixture thereof.

2. The measuring transformer according to claim 1, further including a controlled device for providing and maintain a specific working temperature for said two oxygen sensors.

3. The measuring transformer according to claim 1, wherein said the two oxygen sensors are positioned on an electrically insulating substrate by the use of at least one of a thick film and a thin film technology.

4. The measuring transformer according to claim 1, wherein a portion of the titanium is replaced by another tetravalent element, especially silicon (Si), germanium (Ge), zirconium (Zr), tin (Sn), cerium (Ce), or hafnium (Hf).

5. The measuring transformer according to claim 1, wherein the perovskite structure is of the form $ABO_3$ and wherein the stoichiometry of the perovskite structure metal oxides is adjusted so that the atomic ratio of ions at A-locations to ions at B-locations is between 0.7 and 1.3.

6. The measuring transformer according to claim 1, wherein the two resistive oxygen sensors consist of different materials.

* * * * *